United States Patent [19]

Bremer et al.

[11] Patent Number: 5,287,577
[45] Date of Patent: Feb. 22, 1994

[54] APPARATUS AND METHODS FOR ELEVATING A PATIENT TO FACILITATE X-RAY PHOTOGRAPHY

[76] Inventors: Ross L. Bremer, 1107 Margaret St., Jacksonville, Fla. 32204; David A. Clayman, 2730 Forest Cir., Jacksonville, Fla. 32257

[21] Appl. No.: 3,014
[22] Filed: Jan. 11, 1993
[51] Int. Cl.⁵ .................. A47C 27/08; A61G 7/10
[52] U.S. Cl. ........................... 5/644; 5/81.1; 5/454; 5/601
[58] Field of Search ............. 5/601, 644, 81.1, 630, 5/632, 449, 453, 454, 455; 378/209, 177, 178, 208

[56] References Cited

U.S. PATENT DOCUMENTS

| | | | |
|---|---|---|---|
| 1,998,061 | 4/1935 | Wachs | 5/630 |
| 2,099,977 | 11/1937 | Harris | 5/632 |
| 2,324,619 | 7/1943 | Dunn | 5/81.1 |
| 2,521,530 | 9/1950 | McGuffage | 5/630 |
| 3,026,541 | 3/1962 | Murat | 5/81.1 |
| 3,644,949 | 2/1972 | Diamond | 5/630 |
| 3,729,749 | 5/1973 | Rosecrans | 5/632 |
| 3,740,777 | 6/1973 | Dee | 128/845 |
| 3,757,366 | 9/1973 | Sacher | 5/630 |
| 3,935,604 | 2/1976 | Collins | 5/455 |
| 4,024,861 | 5/1977 | Vincent | 5/449 |
| 4,207,633 | 6/1980 | Smith et al. | 5/632 |
| 4,223,474 | 9/1980 | Strauss | 446/221 |
| 4,466,145 | 8/1984 | Jones et al. | 5/625 |
| 4,873,710 | 10/1989 | Lotman | 5/453 |
| 5,016,268 | 5/1991 | Lotman | 5/601 |
| 5,085,214 | 2/1992 | Barrett | 128/845 |
| 5,113,875 | 5/1992 | Bennett | 5/648 |
| 5,166,968 | 11/1992 | Morse | 378/177 |

*Primary Examiner*—Alexander Grosz
*Attorney, Agent, or Firm*—Nixon & Vanderhye

[57] ABSTRACT

An inflatable bladder is formed of translucent material and includes a plurality of longitudinally extending tubes seamed one to the other in side-by-side generally parallel relation. End tubes extend at right angles to the longitudinally extending tubes, with all of the tubes being in fluid communication one with the other. The longitudinally extending tubes and the end tubes are sized and/or connected one to the other such that, upon inflation, the inflated bladder is supported by the inflated end tubes, with the underside of the longitudinally extending tubes elevated above the surface supporting the end tubes sufficiently to define a recess for receiving an X-ray plate or cassette. Manual movement of the patient is entirely avoided.

13 Claims, 4 Drawing Sheets

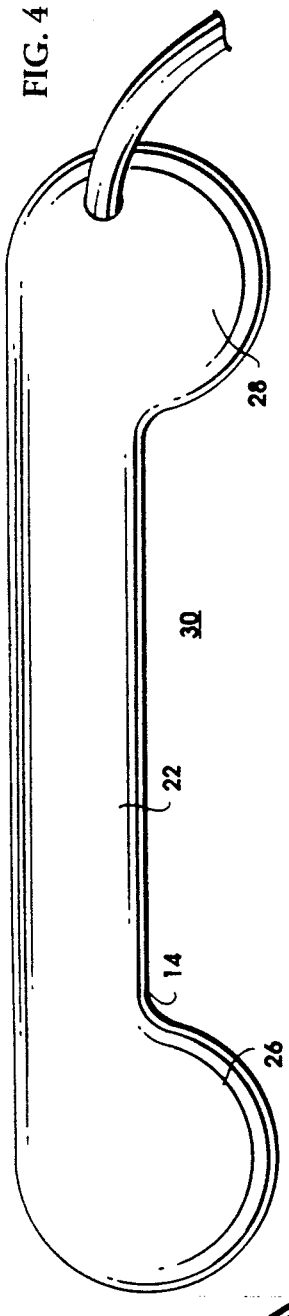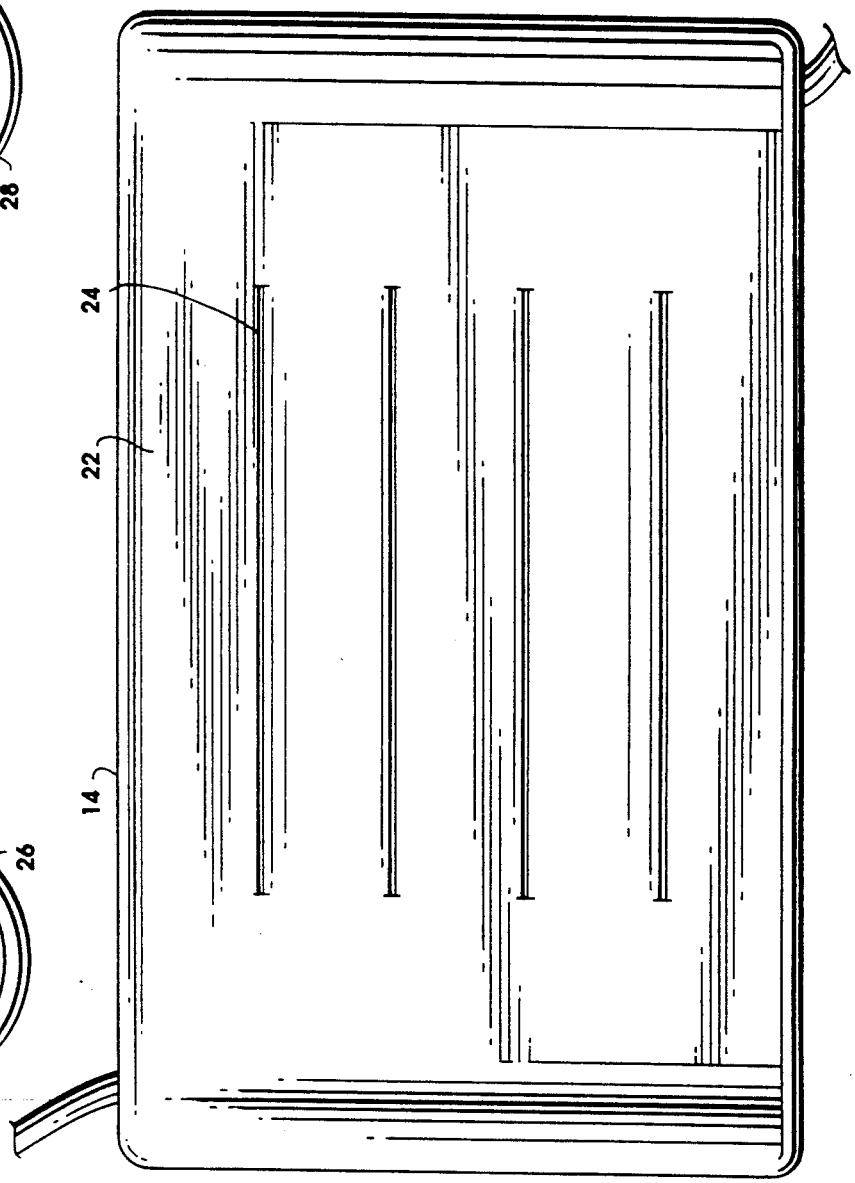

APPARATUS AND METHODS FOR ELEVATING A PATIENT TO FACILITATE X-RAY PHOTOGRAPHY

TECHNICAL FIELD

The present invention relates to apparatus and methods for elevating a patient from a surface sufficient to enable insertion of an X-ray plate underneath the patient for purposes of X-ray photography and particularly relates to an inflatable apparatus for elevating and supporting a patient and defining a recess below the patient for reception of an X-ray plate.

BACKGROUND

Many patients in a hospital setting require frequent X-rays. Some of these patients are virtually immobile. In order to obtain an X-ray of the patient, the patient frequently must be manually lifted by two or more individuals or log-rolled along the bed in order that an X-ray plate or cassette can be inserted below the patient, usually in the region to underlie the patient's chest. Movement of the patient is oftentimes risky from the standpoint of the patient's medical condition and, of course, the necessity to employ two or more individuals to move the patient whereby the X-ray plate or cassette can be inserted and removed after the X-ray has been taken increases the costs and involves substantial manual labor.

DISCLOSURE OF THE INVENTION

In accordance with the present invention, and to entirely eliminate manual movement of the patient for purposes of positioning the the patient for an X-ray, there is provided an inflatable bladder or mat formed of a radiolucent material so that X-rays may be taken through the mat. More particularly, the apparatus preferably comprises a plurality of longitudinally extending, generally parallel side-by-side inflatable tubes. Transversely extending tubes are also provided at right angles to the longitudinally extending tubes and at the opposite ends of the mat. The tubes preferably lie in fluid communication one with the other. An inflation valve is placed on one of the tubes. Accordingly, the tubes can be inflated by coupling a pump to the inflation value for supplying the tubes with air under pressure.

The end tubes are formed and connected to the longitudinally extending tubes such that, upon inflation of the bladder, the end tubes have portions which extend below the undersides of the longitudinally extending tubes. With this configuration, and upon inflation, the end tubes define a recess with the undersides of the longitudinally extending tubes and the underlying surface, typically a bed, on which the bladder is situated. The recess is accessible from at least one side of the bladder and has height, length and width dimensions sufficient for receiving an X-ray plate or cassette. That is, the longitudinally extending tubes and the end tubes are sized differently one from the other and connected to one another such that, upon inflation, the longitudinally extending tubes are elevated above the surface on which the bladder is situated to define the recess. Preferably, the recess is accessible from both sides of the bladder, although access from only one side of the bladder is essential.

In a preferred embodiment of the present invention, the tubes are all formed of a radiolucent material. The longitudinally extending tubes may have a diameter of approximately four inches each, with five tubes extending side-by-side. The end tubes may have a diameter in an inflated state of approximately six inches whereby an elevation of at least one inch at the longitudinally extending tubes above the lower surface of the transversely extending tubes may be effected by inflating the bladder. Preferably, the longitudinally extending tubes are coupled to the end tubes adjacent their upper side such that upon inflation a recess at least two inches in height is formed. The bladder is dimensioned for disposition under the upper torso area of the patient and thus may have dimensions on the order of about 20×34 inches, with five longitudinally extending tubes four inches in diameter and two end tubes six inches in diameter. Upon inflation, a recess having dimensions on the order of at least 1×17×20 inches is formed and which recess is sufficient for the insertion of an X-ray plate or cassette below the patient.

The inflatable bladder or mat may be disposed on top of a bedsheet or below a bedsheet, provided access to the recess formed by the bladder upon inflation is available. In most hospital settings, a vacuum source is available in the hospital room. Thus, in a preferred embodiment of the present invention, a vacuum-powered pump is provided for supplying air under pressure to the inflation valve of the bladder. A foot-operated valve may be provided between the vacuum outlet source and the vacuum-powered pump so that a single individual may operate the bladder, insert the X-ray plate or cassette, take the X-ray and deflate the bladder. It will therefore be appreciated that the services of only one individual are necessary and that the patient can remain substantially immobile during the procedure necessary to take the X-ray.

In a preferred embodiment according to the present invention, inflatable apparatus is provided for elevating a patient from a surface sufficiently to insert an X-ray plate under the patient, comprising a plurality of generally parallel, longitudinally extending inflatable tubes disposed in side-by-side relation relative to one another, a pair of inflatable end tubes at the respective opposite ends of the plurality of tubes and extending laterally thereof, the end tubes having a shape, when inflated, such that portions of the end tubes lie below the undersides of the plurality of tubes to define a recess between the end tubes, the undersides of the plurality of tubes and the surface accessible from at least one side of the apparatus and sufficient in size to receive an X-ray plate and means for inflating the tubes, the tubes being formed of a radiolucent material.

In a further preferred embodiment according to the present invention, there is provided a method of elevating a patient from a surface without manually lifting the patient to locate an X-ray plate under the patient, comprising the steps of locating an inflatable mat on the surface, the mat having inflatable longitudinally extending side-by-side generally parallel tubes and inflatable end tubes extending generally perpendicular to the longitudinally extending tubes, placing a patient above the uninflated mat, inflating the mat to elevate the patient relative to the surface including inflating the end tubes to elevate the longitudinally extending tubes above the surface to define a recess below the longitudinally extending tubes between the longitudinally extending tubes and the surface accessible from one side of the mat and inserting an X-ray plate into the recess for taking an X-ray picture.

Accordingly, it is a primary object of the present invention to provide novel and improved apparatus and methods for elevating a patient above a surface to enable insertion of an X-ray plate or cassette below the patient and the taking of an X-ray.

BRIEF DESCRIPTION OF THE DRAWING

FIG. 1a is a perspective view illustrating a foot pump for inflating the bladder or mat illustrated in FIG. 1;

FIG. 4 is a side elevational view of the bladder;

FIG. 5 is a top plan view thereof;

BEST MODE FOR CARRYING OUT THE INVENTION

Reference will now be made in detail to a present preferred embodiment of the invention, an example of which is illustrated in the accompanying drawings.

Figure 1:
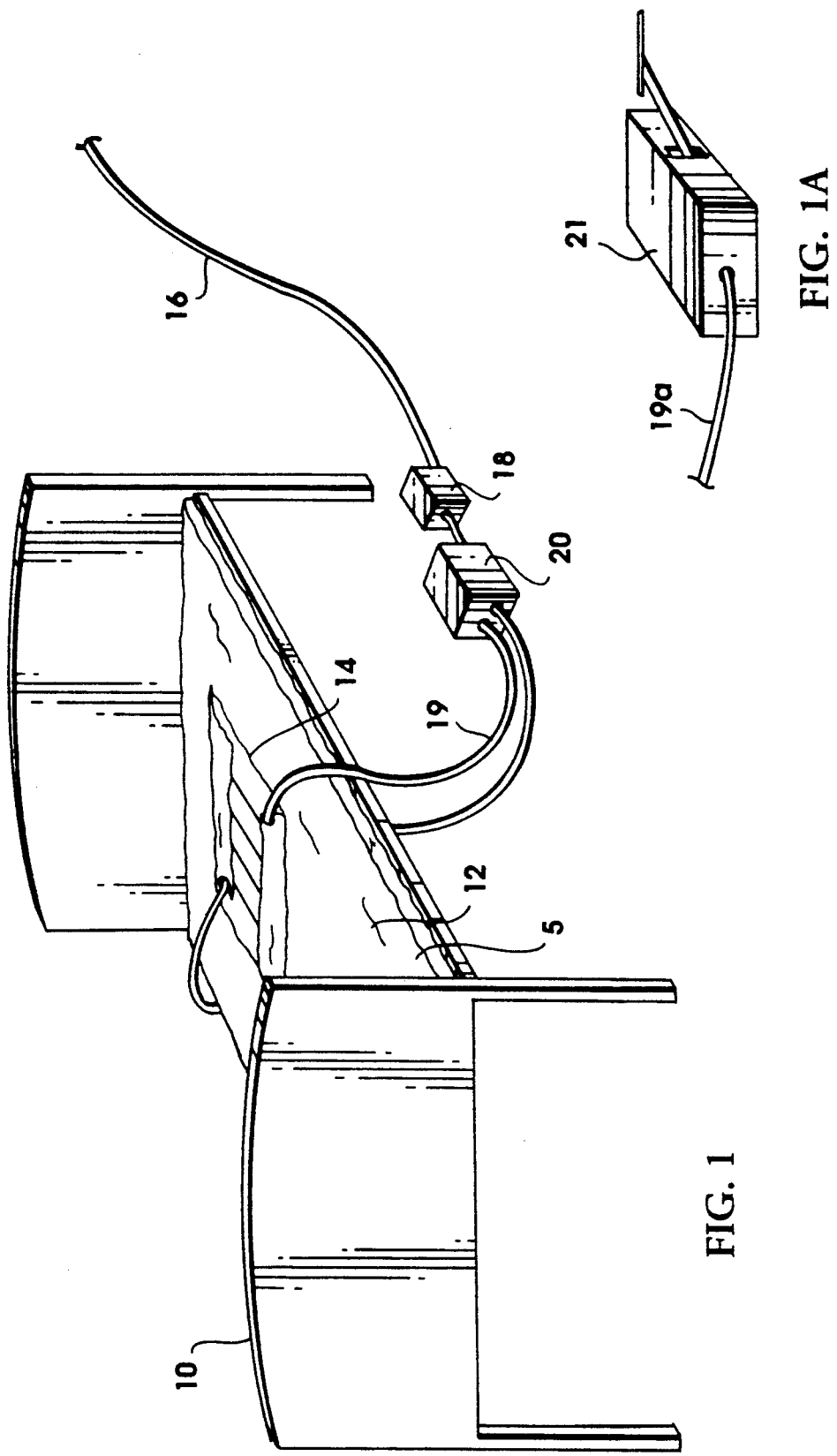
FIG. 1 is a perspective view of a bed illustrating a bladder or mat constructed in accordance with the present invention and disposed on the bed.
Figure 2:
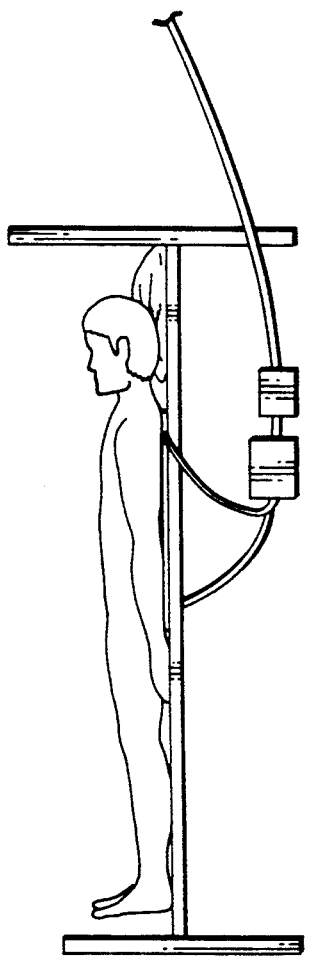
FIGS. 2 and 3 are schematic side elevational views of a patient lying on a bed with the bladder disposed below the patient in deflated and inflated conditions, respectively.
Figure 3:
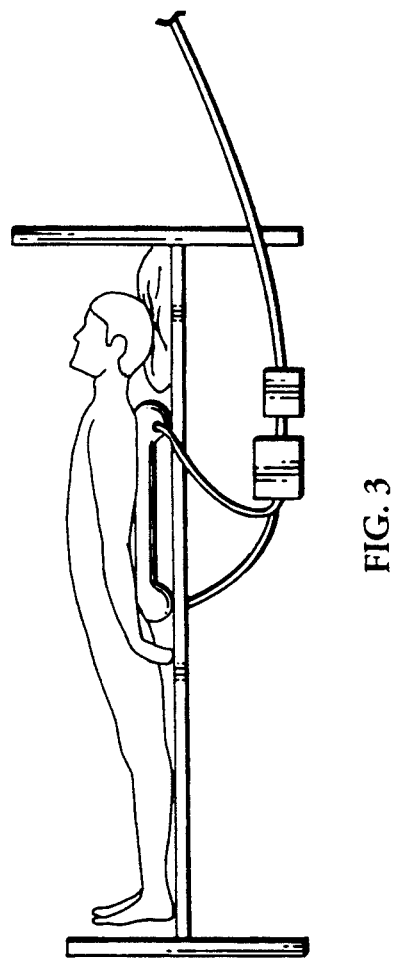

Referring now to the drawings, particularly to FIG. 1, there is illustrated a bed 10 on which a patient, not shown in this Figure but shown in FIGS. 2 and 3, may recline on a surface S, i.e., the upper face of a mattress 12. A bladder or mat constructed in accordance with the present invention is disposed in an uninflated condition, as illustrated, on surface S. For purposes which will become clear from the ensuing description, a vacuum line 16 may be coupled at one end to a source of vacuum, not shown. The opposite end of line 16 is coupled to a foot-operated valve 18, in turn coupled to a vacuum-powered pump 20 for supplying air under pressure via an air feed lines 19 to mat 14 whereby mat 14 may be inflated. Two air feed lines 19 are illustrated to provide a substantial volume of air in a short period of time. Alternately, a foot-operated manual pump 21 may be provided, for example, as illustrated in FIG. 1a, for manually feeding air to the mat via air feed line 19a. This is especially useful in those environs where a source of vacuum may not be available.

Referring now to a first embodiment of the present invention illustrated in FIGS. 4 and 5, there is provided a plurality of longitudinally extending inflatable tubes 22 which are joined together in side-by-side relation by seams 24. In this configuration, there are five longitudinally extending, side-by-side generally parallel tubes. End tubes 26 and 28 are disposed at respective opposite ends of the bladder 14 and extend transversely of the bladder, i.e., normal or perpendicular to the longitudinal extend of tubes 22. The tubes lie in fluid communication one with the other whereby inflation or deflation of one tube correspondingly inflates or deflates the remaining tubes.

It will be appreciated from a review of FIG. 4 that the diameter of the longitudinally extending tubes 22 is less than the diameter of the laterally or transversely extending tubes 26 and 28. Moreover, in this particular form, the longitudinally extending tubes 22 are disposed along and connected to upper portions of the end tubes 26 and 28. Consequently, upon inflation of the bladder 14, the longitudinally extending tubes 22 are spaced above depending or lower inflated portions of the end tubes 26 and 28. By forming the longitudinally extending tubes 22 of a different diameter in comparison with the end tubes 26 and 28 and/or connecting the tubes 22 at an elevated location along the end tubes 26 and 28, it will be appreciated that a recess 30 is defined below the undersides of tubes 22 and between the depending lower portions of end tubes 26 and 28. With the bladder 14 resting on a surface, such as the upper surface of the bed illustrated in FIG. 1, it will be appreciated that the recess 30 is open along its opposite sides. The construction of the mat is such that the recess defined by the tubes 22, 26 and 28 is of sufficient size to receive an X-ray plate or cassette between the opposite depending lower portions of end tubes 26, 28, below the undersides of tubes 22 and above the surface S on which the bladder 14 is disposed. For example, the recess may have a minimum dimension of approximately 1 × 17 × 20 inches in order to receive the X-ray plate or cassette. In the preferred form, the longitudinal tubes are approximately four inches in diameter, while the end tubes are approximately six inches in diameter providing a recess height of about two inches where the upper surfaces of the tubes lie flush with one another. While the bladder is illustrated with the recess open along both sides thereof, it will be appreciated that access to the underside of tubes 22 is only necessary from one side of the bladder and therefore the opposite side may be closed off if desired.

It will also be appreciated that the bladder or mat 14 is formed of a radiolucent material. Materials such as a vinyl-impregnated fabric may be employed in the manufacture of the bladder. With this type of material, the seams may be formed by ultrasonic welding.

Figure 6:
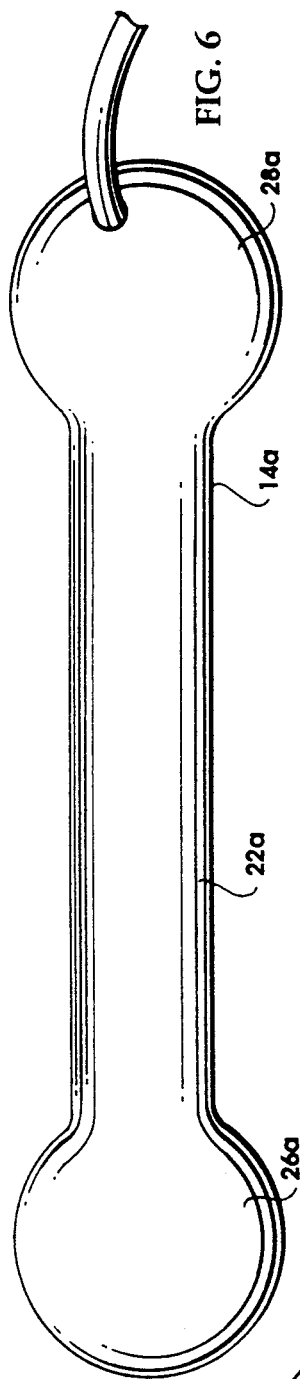
FIG. 6 is a side elevational view of a second embodiment of a bladder constructed in accordance with the present invention.
Figure 7:
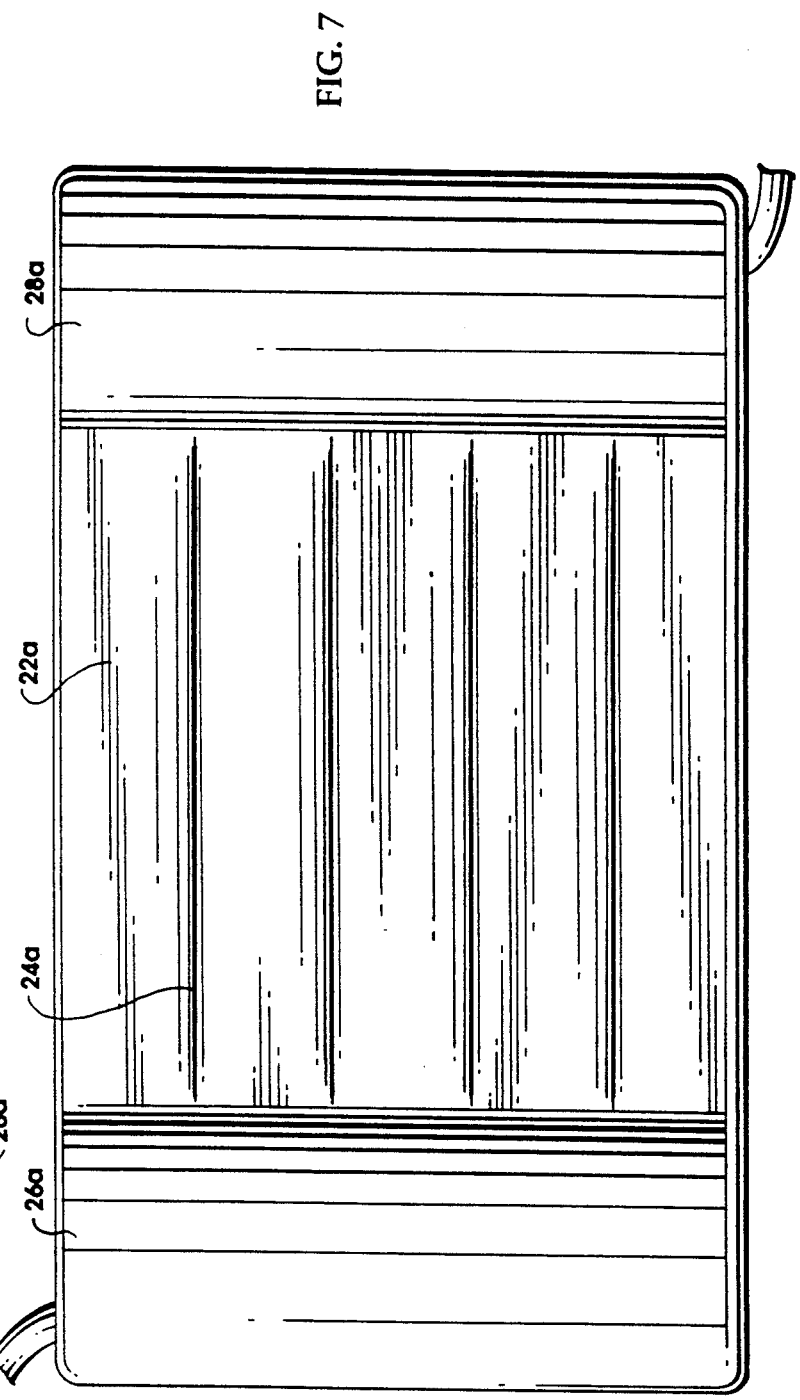
FIG. 7 is a top plan view thereof.

Referring now to the embodiment hereof illustrated in FIGS. 6 and 7, wherein like reference numerals are applied to like parts, followed by the suffix a, there is illustrated a bladder or mat 14a having a plurality of longitudinally extending side-by-side generally parallel tubes 22a, the tubes being seamed one to the other along seam lines 24a. End tubes 26a and 28a are provided in communication with the tubes 22a, the end tubes extending transversely or at right angles to the longitudinally extending tubes 22a. The tubes 22a, 26a and 28a lie in fluid communication one with the other with one of the tubes, for example, tube 28a, having an inflation valve for connection to an air inflation line.

With reference to FIG. 6, it will be appreciated that when the bladder or mat 14a is inflated, it assumes a substantially dumbbell-shaped configuration in side elevation. In that configuration, the smaller-diameter tubes, for example, on the order of four inches in diameter, are spaced centrally of the height of the end tubes 26a and 28a, which are preferably six inches in diameter. In that configuration, the axes of the tubes lie in a common plane and the undersides of the tubes 22a are spaced at least one inch above the surface on which the inflated bladder is situated. This, as in the previous embodiment, affords a recess of a size sufficient to receive an X-ray plate or cassette below the bladder and above the surface.

It will be appreciated that in both configurations, the material forming the tubes is a translucent material which does not in any way interfere with the taking of X-ray photographs.

Referring now to FIGS. 1, 2 and 3, it will be appreciated that the bladder 14 can be disposed on the surface S in a deflated condition, e.g., at a location underlying the upper torso area of the patient to be situated on the surface. The bladder can be located underneath or above the sheets and can be lined with soft absorbent material, as necessary or desirable. With the patient reclining on the surface and bladder, as illustrated in FIG. 2, and when it is desirable to take an X-ray, an individual may simply operate the foot-operated valve 18 to operate the vacuum-operated air pump 20. As the bladder is inflated, it will be appreciated that the air flowing into the inflation tubes intercommunicates among the various tubes such that the pressure is equally distributed within the bladder. By pressurizing the bladder, it will be seen, as illustrated in FIG. 3, that the upper torso of the individual rises from surface S as the bladder inflates and the upper surface thereof is elevated above the surface S of the bed. Note also that the undersurface of the longitudinally extending tubes 22 are spaced by the end tubes 26 and 28 above the surface S, leaving a recess 30 accessible from one or both sides of the bladder. When the bladder is fully inflated, the recess is of a size sufficient to receive a standard X-ray plate or cassette. Once the cassette is in position, the X-ray may be taken. After the X-ray has been taken, the foot-operated valve may be operated to deflate the bladder through an exhaust line whereby the patient and bladder return to their original positions. Note that, not only is the patient elevated by the air-inflated bladder sufficiently to enable the X-ray plate or cassette to be placed below the patient, but also that such elevation is accomplished by a single individual without manual manipulation of the patient. Also, because of the radiolucent material from which the bladder is made, the X-rays are readily taken without interference.

While the invention has been described with respect to what is presently regarded as the most practical embodiment thereof, it will be understood by those of ordinary skill in the art that various alterations and modifications may be made which nevertheless remain within the scope of the invention as defined by the claims which follow.

What is claimed is:

1. Inflatable apparatus for elevating a patient from a surface sufficiently to insert an X-ray plate under the patient, comprising:

a plurality of generally parallel, longitudinally extending inflatable tubes disposed in side-by-side relation relative to one another;

a pair of inflatable end tubes at the respective opposite ends of said plurality of tubes and extending laterally thereof, said end tubes having a shape, when inflated, such that portions of said end tubes lie below the undersides of said plurality of tubes to define a recess between said end tubes, the undersides of said plurality of tubes and the surface accessible from at least one side of said apparatus and sufficient in size to receive an X-ray plate; and means for inflating said tubes, said tubes being formed of a radiolucent material.

2. Apparatus according to claim 1 wherein said recess is accessible through a side of said apparatus opposite said one side.

3. Apparatus according to claim 1 wherein said recess has dimensions at least as great as 1×17×20 inches.

4. Apparatus according to claim 1 wherein said inflating means comprises an air inflation valve carried by one of said tubes and means affording fluid communication between said tubes and said valve.

5. Apparatus according to claim 1 wherein said longitudinal and transversely extending tubes have diameters of about four and six inches, respectively.

6. Apparatus according to claim 1 wherein said recess has dimensions at least as great as 1"×17"×20", said inflating means comprising an air inflation valve carried by one of said tubes and means affording fluid communication between said tubes and said valve.

7. Apparatus according to claim 6 wherein said recess is accessible through a side of said apparatus opposite said one side.

8. Apparatus according to claim 7 wherein said longitudinal and transversely extending tubes have diameters of about four and six inches, respectively.

9. Apparatus according to claim 1 wherein said inflating means includes a foot-operated pump for manually inflating said tubes.

10. A method of elevating a patient from a surface without manually lifting the patient to locate an X-ray plate under the patient, comprising the steps of:

locating an inflatable mat on the surface, said mat having inflatable longitudinally extending side-by-side generally parallel tubes and inflatable end tubes extending generally perpendicular to said longitudinally extending tubes;

placing a patient above the uninflated mat;

inflating the mat to elevate the patient relative to said surface including inflating the end tubes to elevate the longitudinally extending tubes above the surface to define a recess below the longitudinally extending tubes between said longitudinally extending tubes and the surface accessible from one side of said mat; and inserting an X-ray plate into said recess for taking an X-ray picture.

11. A method according to claim 10 including the steps of, after inserting the X-ray plate, obtaining an X-ray picture of the patient and deflating said mat.

12. A method according to claim 10 wherein the step of inflating includes manually operating a pump.

13. A method according to claim 10 wherein the step of inflating includes manually operating a foot pump for pumping air into said mat.

* * * * *